United States Patent [19]

Schuster et al.

[11] Patent Number: 4,672,841
[45] Date of Patent: Jun. 16, 1987

[54] MEASURING HEAD FOR MEASURING THE POROSITY OF A MOVING STRIP

[75] Inventors: Hans K. Schuster, Bruckmühl; Jens-Peter Heins, Feldkirchen-Westerham; Bernhard Gockel, Germering; Holger Schmidt, Munich, all of Fed. Rep. of Germany

[73] Assignee: Gessner & Co. GmbH, Mangfall, Fed. Rep. of Germany

[21] Appl. No.: 882,089

[22] Filed: Jul. 3, 1986

[30] Foreign Application Priority Data

Nov. 6, 1985 [DE] Fed. Rep. of Germany ....... 3539320

[51] Int. Cl.⁴ ............................................. G01N 15/08
[52] U.S. Cl. ......................................... 73/38; 73/37.7; 226/97
[58] Field of Search ............... 73/38, 37.7, 37.6; 226/97

[56] References Cited

U.S. PATENT DOCUMENTS

| | | |
|---|---|---|
| 3,268,222 | 8/1966 | Off .................................... 226/97 X |
| 3,371,518 | 3/1968 | Keyes .................................. 73/38 |
| 3,466,925 | 9/1969 | Ziegenhagen et al. ................ 73/38 |
| 4,311,037 | 1/1982 | Gotchel et al. ................... 73/37.7 X |
| 4,471,649 | 9/1984 | Cronshaw .............................. 73/38 |
| 4,505,412 | 3/1985 | Reba ................................ 226/97 X |

*Primary Examiner*—Stewart J. Levy
*Assistant Examiner*—Joseph W. Roskos
*Attorney, Agent, or Firm*—Louis Orenbuch; George Greenfield

[57] ABSTRACT

The invention relates to a measuring head for measuring the porosity of a moving strip of porous material. The measuring chamber of the measuring head is covered by a measuring plate in which measuring openings are provided. For porosity measurement, air is sucked in through the porous strip and the measuring openings into the measuring chamber. The amount of air flowing into the measuring chamber is measured by a measuring arrangement connected to the measuring air connector and serves as a measure of the porosity of the strip. The measuring plate is surrounded by a guide plate which partially overlaps a blowing ring. The guide plate and blowing ring together form a blowing slot surrounding the measuring plate, the blow-out opening of which is directed outwardly and tangentially to the lower surface of the moving strip. The necessary blowing air is introduced via a connector into an annular channel, which is formed from a semi-circular groove in the blowing ring and merges into the blowing slot. The blowing air flowing horizontally from the blow-out opening produces a reduced pressure between the lower surface of the moving strip and the curved upper surface of the blowing ring. As a result of this reduced pressure, the strip is pressed onto the edge of the guide plate so that the measuring chamber is laterally sealed and air can flow in only through the measuring openings. A filter can be provided between the measuring openings in the meauring plate and the measuring air connector. An additional suction connector enables cleaning of the filter and of the measuring chamber by means of cleaning air introduced through the measuring air connector.

19 Claims, 5 Drawing Figures

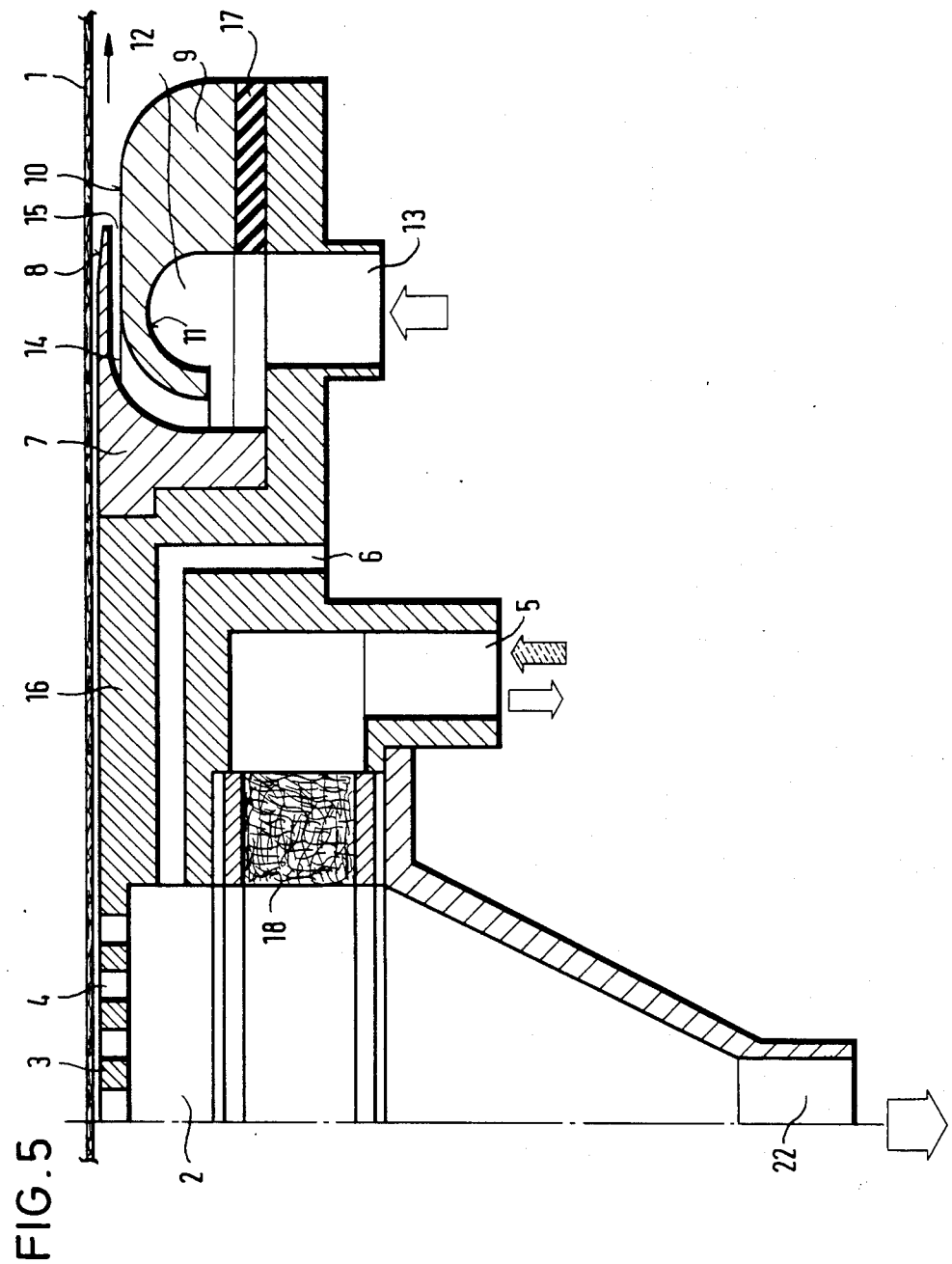

MEASURING HEAD FOR MEASURING THE POROSITY OF A MOVING STRIP

The invention relates to a measuring head for measuring porosity of a moving strip of porous material, comprising a measuring chamber in which reduced pressure is present, a measuring plate covering this measuring chamber, across which plate the strip is moved, measuring openings provided in this measuring plate, via which air is sucked in through the porous strip, a measuring air connector, through which the sucked in air is sucked from the measuring chamber and a device for sucking the strip onto the edge of the measuring plate.

Such a measuring head is employed in the porosity measurement of the moving strip. Particularly with papers, for example filter papers, and web materials, the porosity is an important quality parameter. Its continuous monitoring by means of an on-line measuring method, for example for monitoring and controlling the manufacturing process, is for that reason of great importance. For trouble-free porosity measurement, the upper edge of the measuring chamber must be closed laterally against the strip moving there-across in a manner which is as air-tight as possible so that the only air gaining entry into the measuring chamber is sucked in through the porous strip itself. For this purpose, the strip sliding across the measuring head must be pressed onto the edge of the measuring plate.

In the measuring head for porosity measurement known from U.S. Pat. No. 3,466,925, around the measuring openings provided in the measuring plate additional holes are arranged in a plurality of concentric rings, through which special suction air is sucked. The strip moved across the measuring head is thus sucked onto the edge of the measuring plate. In order to achieve trouble-free sealing between the moving strip and the fixed measuring head, considerable suction pressure is required. The porous strip which is usually freshly manufactured is for that reason pressed with relatively high surface pressure onto the edge of the measuring plate and rubs across the measuring head. In this connection, there is a great danger that fibres will loosen from the webbing texture which is still not completely stabilized, and will either remain stuck on the strip itself and reduce the quality of the finished strip, or, as a result of the measuring vacuum, will enter the measuring chamber and there lead to blockages causing severe disturbance to the porosity measurement.

It is for that reason an object of the present invention to improve the measuring head of the type described in the introduction in such manner that the described disadvantages are prevented; in particular the strip moved across the measuring plate is to be loaded as little as possible, an improved sealing between the measuring chamber and the strip and thus improved measuring precision is to be achieved.

In the solution of this problem, the measuring head according to the invention has a blowing slot surrounding the measuring plate with an outwardly directed blow opening tangential to the lower surface of the strip.

In the measuring head according to the invention, instead of the suction air employed in the conventional measuring heads, air blown tangentially against the lower side of the moving strip is used to suck the strip onto the edge of the measuring plate. The air flowing in this manner between the lower surface of the strip and the outer edge of the measuring head produces a reduced pressure which sucks the strip onto the edge of the measuring plate and thus effects lateral sealing of the measuring chamber. In this way, the strip moving across the measuring head is not—as in conventional devices provided with suction holes at quite specific positions—violently loaded with suction force, but the blown air blowing along the lower surface of the strip approximately parallel thereto develops its suction effect continuously and increasingly in the direction of the measuring plate. The mechanical loading of the sensitive strip of porous material is therefore substantially lower than in the already known measuring heads. An additional advantage consists in that any loose fibres sticking to the lower surface of the strip, or particles of dirt are not sucked into the measuring head, but are blown away from the outer surface of the strip. The interior of the measuring head and in particular the measuring chamber remain for this reason substantially free of contamination and deposits. Since the moving strip passes a zone of reduced pressure before reaching the actual measuring openings, a pre-evacuation of the cavities in the porous material takes place, whereby false measurements as a result of trapped air reaching the measuring chamber are prevented. The measuring head according to the invention therefore permits improvement of the precision of the porosity measurement.

Expediently, the blowing slot tapers towards the blow-out opening in order to achieve an outlet speed of the blown air which is sufficiently high to produce sufficient reduced pressure.

In a preferred embodiment of the measuring head according to the invention, an annular channel surrounding the measuring chamber, which merges into the surrounding blowing slot, serves for uniform supply of blowing air to the blowing slot, which is supplied via at least one connection member discharging into this annular channel from a suitable blower.

In a further advantageous embodiment of the invention, the measuring plate is surrounded by a guide plate which extends to the blow-out opening. This guide plate effects guidance of the moving strip in the vertical direction so that the guide plate is always completely covered over. Expediently, the upper surfaces of the measuring plate and the guide plate abut, and thus form a common flat surface, across which the strip can slide without obstruction. A slight incline of the guide plate at its periphery facilitates passage of the moving strip onto the measuring head.

In a preferred embodiment of the invention, the annular channel for distribution of the blown air is formed substantially from a surrounding blowing ring. Advantageously, this blowing ring has a cross-section in the form approximately of segments of a circle and has on its flat lower surface a semi-circular groove, which forms the annular channel. The rounded contour of the upper surface of the blowing ring assists the formation of the air flow on the periphery of the measuring head which produces the desired reduced pressure. A particularly quiet flat air flow is formed if the blowing ring has on its upper surface a plane flattened region extending parallel to the strip.

In a particularly preferred embodiment, the blowing slot is formed from the lower surface of the guide plate and the upper surface of the blowing ring. Expediently, in this connection the guide plate overlaps approximately half of the blowing ring. If moreover the blowing ring is mounted for vertical displacement, the thickness of the blowing slot can be adjusted in a simple manner by changing the spacing between the blowing ring and the guide plate. In a measuring head constructed in this manner the force with which the moving strip is sucked can be adapted easily to differing measuring conditions and strip materials.

In an expedient further development of the measuring head according to the invention, the measuring plate, guide plate and blowing ring are mounted on a common carrier plate surrounding the measuring chamber. Other methods of construction are however conceivable, in which for example the measuring plate and guide plate are formed in one piece. If an elastic sealing ring is provided between the carrier plate and the blowing ring mounted thereon, the spacing between the blowing ring and the guide plate and thus the thickness of the blowing slot can be adjusted by greater or lesser tightening of the connection elements, the sealing ring giving elastically.

A construction of the measuring openings in the measuring plate in the form of elongate slots which extend parallel to the direction of movement of the moving strip leads to a further reduction of the mechanical attrition of the sensitive strip lower surface.

In an advantageous further development of the invention, on the upper surface of the measuring head, between the measuring openings and the blow-out opening, an additional annular measuring channel is provided, by means of which the reduced pressure occurring directly on the lower surface of the strip can be measured. A reduced pressure measurement at this point is a prerequisite for control of the amount of blown air flowing from the blow-out opening in such manner that the reduced pressure occurring as a result on the lower surface of the strip corresponds approximately to the reduced pressure occurring in the measuring chamber. The pressure fall-off along the strip in the region of the edge of the measuring plate can then not occur, whereby measuring errors as a result of inclined or even laterally directed measuring air flowing through the porous strip are prevented.

In spite of the described cleaning effect of the blowing air passing along the lower surface of the moving strip, the incursion of dust and dirt particles into the sensitive measuring system cannot be completely prevented. It is therefore preferred to employ an embodiment of the measuring head according to the invention in which a filter is arranged in the measuring chamber between the measuring openings provided in the measuring plate and the measuring air connector, to which the necessary measuring arrangements are connected. The precision of the porosity measurement is still further improved by this means. An annular construction of the inserted filter enables low constructional height of the measuring head to be achieved. If, on the other hand, the radius of the measuring head is to be maintained as small as possible, a central arrangement of the measuring air connector on the side lying opposite to the measuring plate is advantageous, the filter then covering the measuring air connector.

In a particularly advantageous embodiment of the invention, an additional suction connector for connection of a suction cleaner is provided on that side of the measuring chamber lying opposite to the measuring plate, and the filter is arranged between this suction connector and the annular suction air connector. For the purpose of cleaning the measuring chamber, in this embodiment the blowing air which is in any case present can be guided counter to the usual flow direction through the measuring air connector to the measuring chamber and after flowing through the filter can be sucked out through the suction connector. The amount of cleaning air is in this connection so chosen that the amount of air sucked by the suction cleaner is larger than the amount of blowing air fed in, whereby it is prevented that the measuring openings in the measuring plate carry counter flow during measuring operations, which could lead to dust or dirt particles being deposited on the inner surface of the measuring plate. Additionally equipping the measuring head with a suction connector thus enables trouble-free cleaning of the measuring chamber in the simplest manner.

A circular configuration of the measuring head according to the invention is particularly preferred such that the blowing slot concentrically surrounds the measuring plate. The rotationally symmetric construction of the measuring head exhibits particularly good aerodynamic properties and is simple and thus can be manufactured inexpensively.

Embodiments of the invention will be described in the following with reference to the accompanying drawings, in which:

FIG. 5 shows a further exemplary embodiment of the measuring head according to the invention, having an annular filter and an additional suction connector for connection of a suction cleaner.

In all Figures, only one half of the rotationally symmetric measuring head is illustrated in vertical section.

Figure 1:
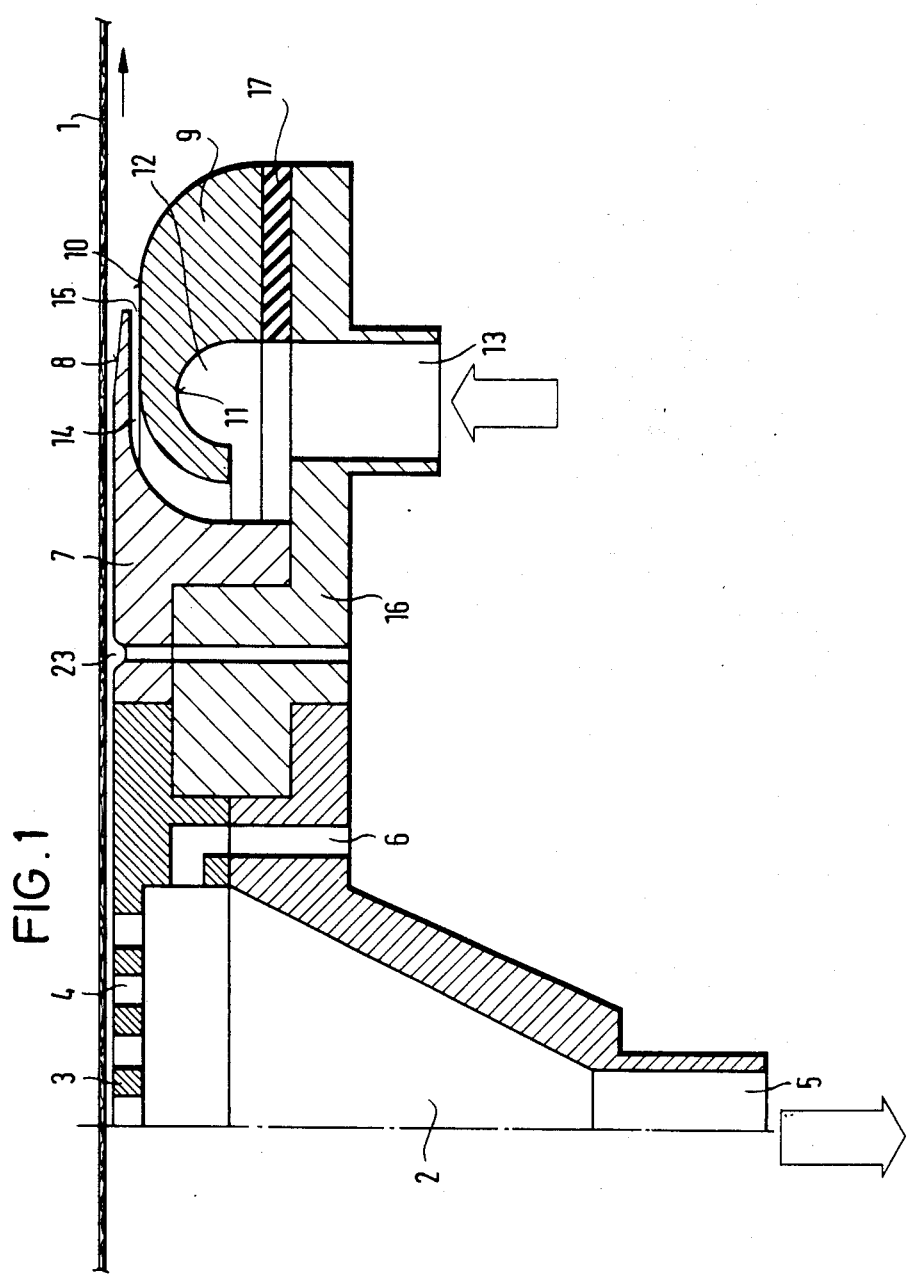
FIG. 1 shows a measuring head according to the invention having a central measuring air connector.

According to FIG. 1, the strip of porous material, the porosity of which is to be measured, moves in the direction indicated by an arrow over the upper surface of the measuring head. The measuring chamber 2 is upwardly covered by a measuring plate 3, in which measuring openings 4 are provided. The measuring chamber 2 discharges downwardly into a central measuring air connector 5, onto which a device, which is not illustrated, is connected for producing a reduced pressure. During the measuring process, air is sucked in through the porous strip 1 and the measuring openings 4 into the measuring chamber 2. The amount of the sucked air, which is measured by means of a suitable measuring arrangement, is a measure of the porosity of the strip 1. The reduced pressure present in the measuring chamber 2, which is maintained as constant as possible during measuring, can be measured separately via a separate measuring channel 6. The round measuring plate 3 is surrounded by a similarly round guide plate 7. The upper surfaces of the measuring plate 3 and the guide plate 7 are in abutting relationship so that they form a common flat surface across which the strip 1 slides. On its outer periphery, the guide plate 7 has a slight incline 8. The guide plate 7 partially overlaps a blowing ring 9, having a cross-section which is approximately a segment of a circle and a plane flattened region 10 on its upper surface lying parallel to the strip 1. On its flat lower surface, the blowing ring 9 has a semi-circular groove 11, which forms an annular channel 12 concentrically surrounding the measuring chamber 2. During the measuring operation, blown air is introduced into the annular channel 12 via a connector 13. The annular channel 12 merges into a blowing slot 14 surrounding the measuring plate 3, the blowing slot 14 being formed by the curved lower surface of the guide plate 7 and the oppositely lying upper surface of the blowing ring 9. The blow-out opening 15 of this blowing slot 14 is directed outwardly and tangential to the lower surface of the moving strip 1. The blowing air streaming therethrough produces a reduced pressure between the lower surface of the strip 1 and the circularly curved outer contour of the blowing ring 9, whereby the strip 1 is pressed onto the edge of the guide plate 7. Any particles adhering to the lower surface of the strip 1 are thereby blown away outwardly. The continuous tapering of the blowing slot 14 to the blow-out opening 15 effects a sufficiently high blow-out speed of the flowing blown air. The measuring plate 3, the guide plate 7 and the blowing ring 9 are mounted together on a circular carrier plate 16. Between this carrier plate 16 and the blowing ring 9 is provided an elastic sealing ring 17. The blowing ring 9 is in this connection mounted for vertical displacement in such manner that the thickness of the blowing slot 14 is adjustable by change of the spacing between the blowing ring 9 and the guide plate 7, the sealing ring 17 being capable of giving elastically.

In the upper surface of the guide plate 7 is provided an annular measuring channel 23 for measuring the reduced pressure occurring on the lower surface of the strip 1.

Figure 2:
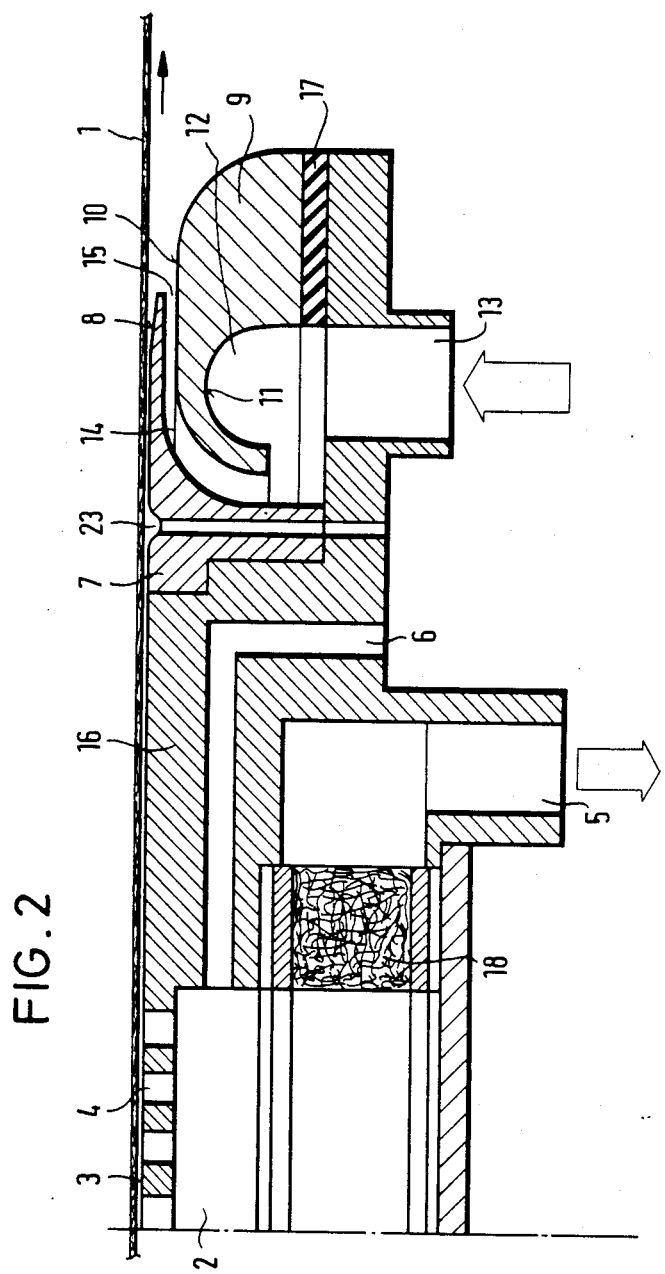
FIG. 2 shows a second embodiment of the measuring head according to the invention having an annular filter.

The measuring chamber 2 of the second exemplary embodiment of the measuring head according to the invention illustrated in FIG. 2 is characterized by an enlarged diameter and simultaneously reduced height. The measuring plate 3 is formed in one piece on the carrier plate 16. In this way, an overall reduced height of the measuring head results. In the measuring chamber 2 is provided an annular filter 18, which is arranged between the measuring openings 4 and the measuring air connector 5. It serves for filtering the measuring air flowing through the measuring chamber 2 in order to protect the sensitive measuring system connected to the measuring air connector 5 from dust and dirt particles.

Figure 3:
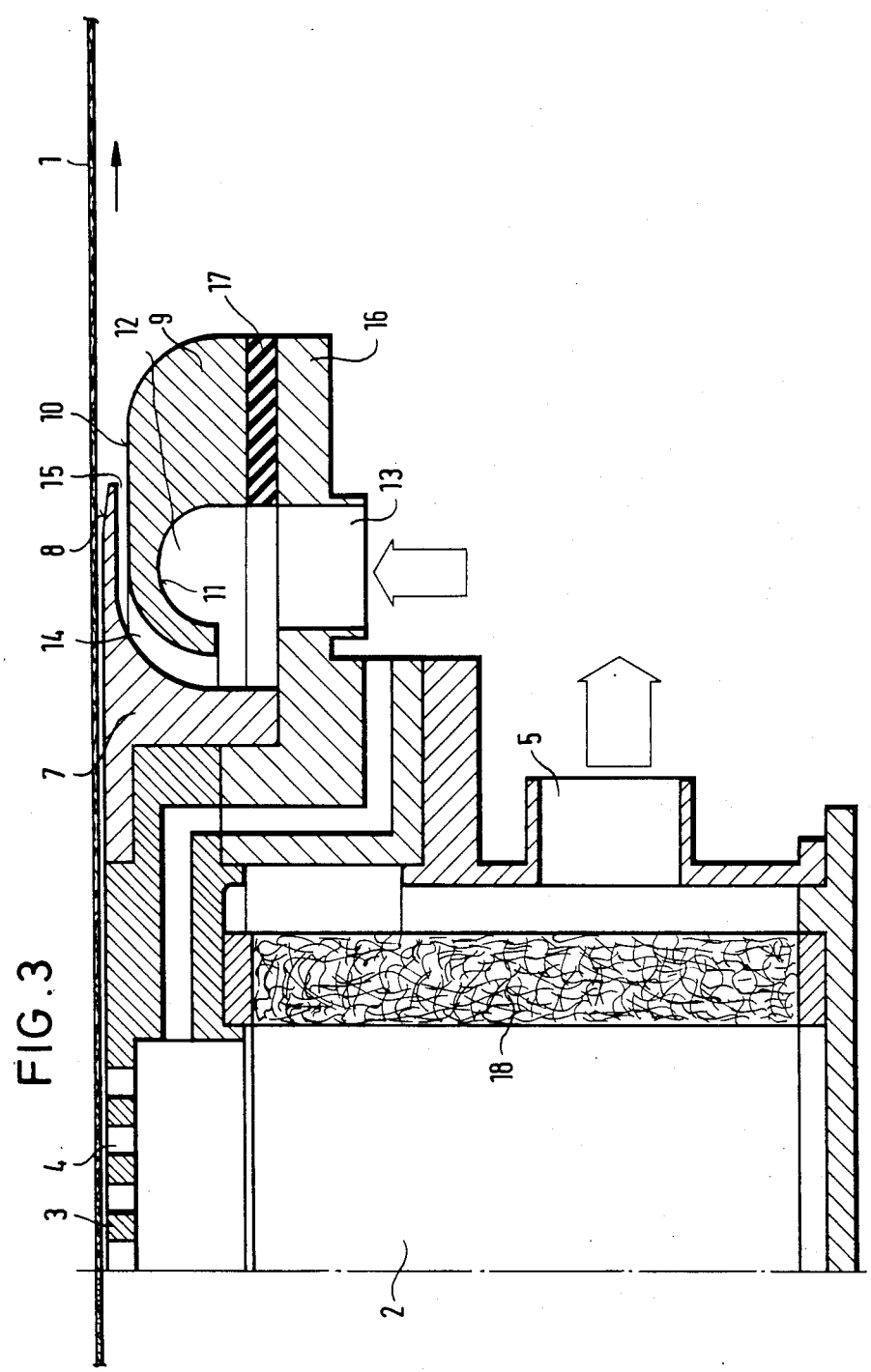
FIG. 3 shows a third embodiment of the measuring head according to the invention having a filter arranged in the measuring chamber in the form of a hollow cylinder.

FIG. 3 shows an embodiment of the measuring head according to the invention, which is distinguished by a substantially enlarged filter 18 in the form of a hollow cylinder.

Figure 4:
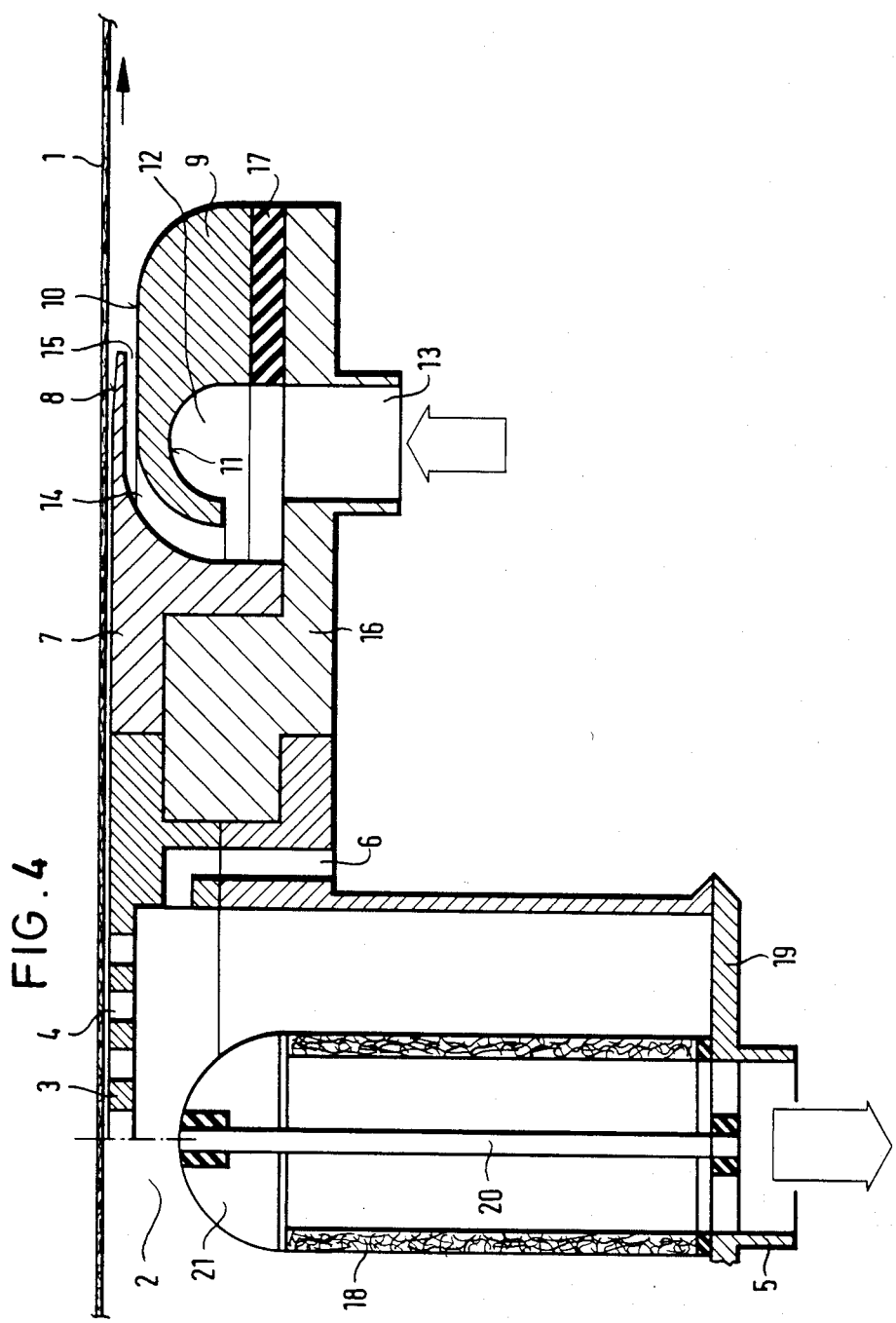
FIG. 4 shows a fourth embodiment of the measuring head according to the invention having a central measuring air connector and an axially arranged filter covering the measuring air connector.

FIG. 4 shows a further exemplary embodiment of the measuring head. The measuring chamber 2 is downwardly closed by a cover 19, in which a central measuring air connector 5 is formed with an annular outlet opening. The cylindrically constructed filter 18 covers the measuring air connector 5 completely. On the inner side of the lid 19 is releasably mounted the filter 18 by means of a central holding rod 20 and a securing cap 21, so that it can easily be replaced.

In the measuring head illustrated in FIG. 5, an additional suction connector 22 is provided on the side of the measuring chamber 2 lying opposite to the measuring plate 3, for connection of a suction cleaner (not illustrated). The filter 18 is located between this suction connector 22 and the measuring air connector 5. For cleaning the filter 18 and the measuring chamber 2, cleaning air is guided via the measuring air connector 5 against the flow direction during measuring operation through the filter 18 into the measuring chamber 2 and is sucked out via the suction connector 22. If the amount of cleaning air introduced is adjusted in such manner that it does not exceed the amount of air sucked out through the suction connector 22, it is ensured that the measuring openings 4 in the measuring plate 3 pass air continuously from the exterior to the interior and not in the reverse direction, so that no dirt or dust can be deposited on the interior of the measuring plate 3.

What is claimed is:

1. In apparatus for measuring the porosity of a moving strip of porous material, where the apparatus is of the kind comprising
   (i) a measuring chamber;
   (ii) a measuring plate covering the measuring chamber, the measuring plate providing a surface for supporting the strip during movement of the strip across the measuring plate, the measuring plate having openings therethrough which enable air to be sucked through the moving porous strip and into the measuring chamber; and (iii) a measuring air connector through which air can be sucked out of the measuring chamber; the improvement for sealing that portion of the moving strip adjacent to or on the periphery of the measuring plate to impede the passage of air except through the porous material situated over and near the the openings in the measuring plate, the improvement comprising
   means forming a blowing slot extending around the measuring plate and providing an outwardly directed blow opening for emitting a stream of air substantially tangentially to the support surface of the measuring plate.

2. The improvement according to claim 1, further including
   means forming a passage connecting the blowing slot with the blow opening, the passage gradually constricting as it nears the blow opening.

3. The improvement according to claim 2, further including
   a guide plate which surrounds and extends the support surface of the measuring plate, the support surface extension of the guide plate extending up to the blow opening.

4. The improvement according to claim 3, wherein
   the measuring plate and the guide plate abut and provide a substantially continuous flat surface that supports the strip as it slides thereover.

5. The improvement according to claim 3, wherein
   the outer edge of the guide plate support surface has a gentle downward slope.

6. The improvement according to claim 3, wherein
   the means forming the connecting passage includes a surface of the guide plate and a surface of the blowing ring confronting and spaced by a gap from said guide plate surface.

7. The improvement according to claim 6, further including
   means enabling the blowing ring to be moved relative to the guide plate whereby the connecting passage gap between the blowing ring and the guide plate may be changed.

8. The improvement according to claim 1, wherein
   the blowing slot has an annular channel surrounding the measuring chamber, and the improvement further comprises
means forming a tapered passage connecting the annular channel with the blow opening whereby air flowing from the annular channel toward the blow opening accelerates as the air approaches the blow opening.

9. The improvement according to claim 8, further including
means providing and air passage into the annular channel for conducting blowing air into the annular channel.

10. The improvement according to claim 8, wherein the means forming the annular channel includes a blowing ring.

11. the improvement according to claim 10, wherein the blowing ring has a semicircular groove therein extending around the ring and forming a domed chamber as part of the annular channel.

12. The improvement according to claim 11, wherein the upper surface of the blowing ring has an annular flat region extending parallel to the support surface of the measuring plate.

13. The improvement according to claim 8, further including
a carrier plate surrounding the measuring chamber, the guide plate and the blowing ring being mounted on the carrier plate.

14. The improvement according to claim 13, further including
an elastic sealing ring situated between the carrier plate and the blowing ring.

15. The improvement according to claim 1, further including
an air filter disposed between the measuring plate and the measuring air connector.

16. The improvement according to claim 15, wherein the air filter is an annular structure.

17. the improvement according to claim 15, wherein the measuring air connector is situated directly below some of the openings in the measuring plate and the passage of air from the measuring chamber to the measuring air connector is through the air filter.

18. The improvement according to claim 1, further including
(a) an annular suction chamber surrounding and laterally offset from the measuring chamber,
(b) an annular filter forming an air permeable wall between the suction chamber and the measuring chamber, and
(c) suction connector means for enabling air to be drawn out of the suction chamber.

19. The improvement according to claim 1, wherein the measuring plate is circular and the blowing slot surrounds and is concentric with the circular measuring plate.

* * * * *